(12) United States Patent
Bachmann et al.

(10) Patent No.: US 8,877,704 B2
(45) Date of Patent: Nov. 4, 2014

(54) ORGANIC COMPOUNDS

(71) Applicant: Givaudan SA, Geneva (CH)

(72) Inventors: Jean-Pierre Bachmann, Wädenswil (CH); Felix Flachsmann, Duebendorf (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 14/051,838

(22) Filed: Oct. 11, 2013

(65) Prior Publication Data
US 2014/0107006 A1  Apr. 17, 2014

(30) Foreign Application Priority Data

Oct. 15, 2012 (GB) .................................. 1218447.9

(51) Int. Cl.
| | |
|---|---|
| *A61Q 13/00* | (2006.01) |
| *C11D 3/50* | (2006.01) |
| *A61K 8/35* | (2006.01) |
| *A23L 1/226* | (2006.01) |
| *C11B 9/00* | (2006.01) |

(52) U.S. Cl.
CPC .............. *C11B 9/0061* (2013.01); *A61K 8/35* (2013.01); *C11D 3/50* (2013.01); *A23L 1/22657* (2013.01)
USPC ................. 512/24; 512/16; 512/20; 510/102; 510/105

(58) Field of Classification Search
USPC .......................... 512/16, 20, 24; 510/102, 105
See application file for complete search history.

(56) References Cited

U.S. PATENT DOCUMENTS 3,068,151 A * 12/1962 Haefele ...................... 424/70.15
2004/0068920 A1 * 4/2004 Steele et al. ................... 44/275

FOREIGN PATENT DOCUMENTS

WO     2011023886 A2     8/2010

OTHER PUBLICATIONS

GB Search report for GB1115444.0 dated Dec. 16, 2011.

* cited by examiner

*Primary Examiner* — Brian P Mruk
(74) *Attorney, Agent, or Firm* — Norris McLaughlin & Marcus PA

(57) ABSTRACT

Disclosed are certain compounds according to the general formula (I)

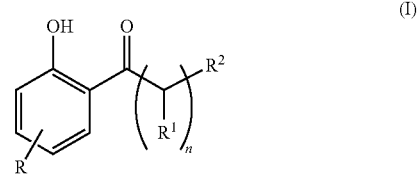

and their use as flavoring and fragrancing compounds, as well as fragranced and flavored compositions comprising the compounds of formula (I), and methods for providing a flavor or fragrance to compositions and articles utilizing the compounds of formula (I).

9 Claims, No Drawings

ORGANIC COMPOUNDS

This application claims priority to GB 1218447.9, filed 15 Oct. 2012. The entire contents of that priority document are herein incorporated by reference.

The present invention relates to certain ortho-hydroxyphenyl aryl ketones possessing odor notes useful for perfumery, which are in the floral, salicylate or green range. This invention relates furthermore to flavor and fragrance compositions and flavored or fragranced articles comprising them.

In the fragrance industry there is a constant demand for new compounds that enhance, modify or improve on odor notes. Surprisingly, it has now been found that certain ortho-hydroxyphenyl aryl ketones of formula (I) as defined below constitute very powerful floral salicylate like odorant.

To the best of our knowledge none of the compounds as defined herein below has been described as flavor or fragrance ingredient nor is there an indication in the literature that these compounds are suitable as fragrance ingredients.

Accordingly, the present invention refers in one of its aspects to the use as flavor or fragrance of a compound of formula (I)

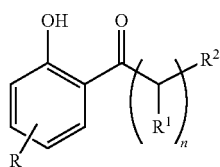

wherein
R is hydrogen or methyl;
n=0 or 2;
$R^1$ is, independently of each other, hydrogen or methyl
$R^2$ is phenyl wherein the ring is optionally substituted with one or two methyl groups, and the compound of formula (I) comprises 13 to 18 carbon atoms, i.e. 13, 14, 15, 16, 17 or 18 carbon atoms.

Non-limiting examples are compounds of formula (I) wherein R and $R^1$ arehydrogen and $R^2$ is phenyl or tolyl (e.g. ortho- or para-tolyl).

Further, non-limiting examples are compounds of formula (I) wherein n is 2 and $R^1$ is hydrogen.

Further, non-limiting examples are compounds of formula (I) wherein R is methyl, $R^2$ is phenyl, n is 0 or 2, and $R^1$ is hydrogen.

Further, non-limiting examples are compounds of formula (I) wherein n is 2, R is hydrogen, $R^2$ is phenyl and one or both $R^1$ are methyl.

Further, non-limiting examples are compounds of formula (I) wherein n is 2, and one $R^1$ is methyl with the proviso that the methyl group is in alpha position to the carbonyl group.

Further, non-limiting examples are compounds of formula (I) wherein n is 2, and one $R^1$ is methyl with the proviso that the methyl group is in beta position to the carbonyl group.

Further, non-limiting examples are compounds of formula (I) selected from (2-hydroxyphenyl)(phenyl)methanone, 1-(2-hydroxyphenyl)-3-(o-tolyl)propan-1-one, 1-(2-hydroxyphenyl)-2-methyl-3-phenylpropan-1-one, 1-(2-hydroxy-5-methylphenyl)-3-phenylpropan-1-one, 1-(2-hydroxyphenyl)-3-phenylbutan-1-one, and 1-(2-hydroxyphenyl)-3-phenylpropan-1-one.

As a further example of the invention's compound, one may cite 1-(2-hydroxyphenyl)-3-phenylpropan-1-one which possesses a floral green odor with some aspects of linden blossom and ylang ylang facets. One may also note that the olfactory impact of said compound lasts for several weeks on blotter, which makes it particularly suitable for use in laundry care products, such as liquid and powder detergents and fabric conditioners, personal care products, such as shampoo, hair conditioners, deodorants and antiperspirants, and home care products, such as all purpose cleaners.

It was also found that in comparison with the corresponding salicylate derivatives, the compounds of formula (I) as hereinabove defined are much more stable in ethanol based products, e.g. products in which ethanol constitutes at least 20% wt/wt of the final product, such as fine fragrance or ethanolic deodorant products and body sprays.

Thus there is provided in a further aspect, a fragranced article, comprising a compound of formula (I) and a consumer product base comprising ethanol.

Surprisingly inventors found that, beside the remarkable odor characteristic, the compounds absorb the UV light over a very broad range (i.e. from 230 to 400 nm, thus covering both, the UV-A and UV-B range), which make them particular suitable for use in fragranced sunscreen products.

The compounds of formula (I) may be used alone, as mixtures thereof, or in combination with a base material. As used herein, the "base material" includes all known odorants or flavors selected from the extensive range of natural products and synthetic molecules currently available, such as essential oils, alcohols, aldehydes and ketones, ethers and acetals, esters and lactones, macrocycles and heterocycles, and nitriles, and/or in admixture with one or more ingredients or excipients conventionally used in conjunction with odorants or flavors in fragrance/flavor compositions, for example, carrier materials, and other auxiliary agents commonly used in the art.

As used herein, "fragrance composition" and "flavor composition" means any composition comprising at least one compound of formula (I) and a base material, e.g. a diluent conventionally used in conjunction with odorants, such as dipropylene glycol (DPG), isopropyl myristate (IPM), triethyl citrate (TEC), alcohol (e.g. ethanol), and propylene glycol (PG), triacetine, and/or a known odorant.

The following list comprises examples of known odorant molecules, which may be combined with the compounds of formula (I):

essential oils and extracts, e.g. castoreum, costus root oil, oak moss absolute, geranium oil, tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™ (3-methyl-5-(2,2,3-trimethyl-3-cyclopenten-1-yl)-4-penten-2-ol), eugenol, farnesol, geraniol, Super Muguet™ (6-ethyl-3-methyl-5(6)-octen-1-ol), linalool, menthol, nerol, phenylethyl alcohol, rhodinol, Sandalore™ (5-(2,2,3-trimethyl-3-cyclopentyl)-3-methylpentan-2-ol), terpineol or Timberol™;

aldehydes and ketones, e.g. Azurone® (7-(3-methylbutyl)-1,5-benzodioxepin-3-one), anisaldehyde, α-amylcinnamaldehyde, Georgywood™ (2-acetyl-1,2,3,4,5,6,7,8-octahydro-1,2,8,8-tetramethylnaphthalene), hydroxycitronellal, Iso E® Super, Isoraldeine®, Hedione®, Lilial®, maltol, methyl cedryl ketone, methylionone, rotundone, verbenone or vanillin;

ethers and acetals, e.g. Ambrox™, geranyl methyl ether, rose oxide or Spirambrene™ ((1R,3S,6S)-rel-2',2',3,7, 7-pentamethyl-spiro[bicyclo[4.1.0]heptane-2,5-[1,3] dioxane]);

esters and lactones, e.g. benzyl acetate, Cedryl acetate, γ-decalactone, Helvetolide®, γ-undecalactone or vetivenyl acetate;

macrocycles, e.g. Ambrettolide, ethylene brassylate or Exaltolide®;

heterocycles, e.g. isobutylquinoline;

nitriles, e.g. Peonile® (2-cyclohexylidene-2-phenylacetonitrile) or Violet Nitrile® (nona-2,6-dienenitrile).

The compounds according to formula (I) may be used in a broad range of fragranced articles, e.g. in any field of fine and functional perfumery, such as perfumes, air care products, household products, laundry products, body care products and cosmetics. The compounds can be employed in widely varying amounts, depending upon the specific article and on the nature and quantity of other odorant ingredients. The proportion is typically from 0.0001 to 5 weight percent of the article. In one embodiment, compounds of the present invention may be employed in a fabric softener in an amount of from 0.0001 to 0.2 weight percent. In another embodiment, compounds of the present invention may be used in fine perfumery in amounts from 0.001 to 10 weight percent (e.g. up to about 5 weight percent), more preferably between 0.02 and 4 weight percent. However, these values are given only by way of example, since the experienced perfumer may also achieve effects or may create novel accords with lower or higher concentrations.

The compounds as described hereinabove may be employed in a consumer product base simply by directly mixing at least one compound of formula (I), or a fragrance composition comprising said compound, with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, the invention additionally provides a method of manufacturing a fragranced article, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactory acceptable amount of at least one compound of the present invention as hereinabove described the odor notes of a consumer product base will be improved, enhanced, or modified.

Thus, the invention furthermore provides a method for improving, enhancing or modifying a consumer product base by means of the addition thereto of an olfactorily acceptable amount of at least one compound of formula (I).

The invention also provides a fragranced or flavoured article comprising:
a) as odorant at least one compound of formula (I); and
b) a consumer product base.

As used herein, "consumer product base" means a composition for use as a consumer product to fulfill specific actions, such as cleaning, softening, and caring or the like. Examples of such products include fine perfumery, e.g. perfume and eau de toilette; laundry care, such as fabric conditioner, liquid and powder detergents, tumble dryer sheet; body care products, such as shampoo, hair conditioner, body soap, liquid soap, shower gel, body deodorant, and sunscreen products; beauty care (cosmetics), such as skin lotion, skin cream, and vanishing créme; air care and household products in general, such as detergent for dishwasher, and surface cleaner. This list of products is given by way of illustration and is not to be regarded as being in any way limiting.

The compounds of formula (I) may be prepared by Fries-rearrangement of the corresponding phenyl esters (III), as depicted in Scheme 1. The ratio between desired products (I) and the undesired p-substituted products (II) depends on the respective starting materials as well as solvent and temperature. A person skilled in the art will find the ideal reaction conditions (e.g. selection of the catalyst, solvent and/or reaction temperature) to obtain the desired compound of formula (I) with high yields and purity.

Scheme 1:

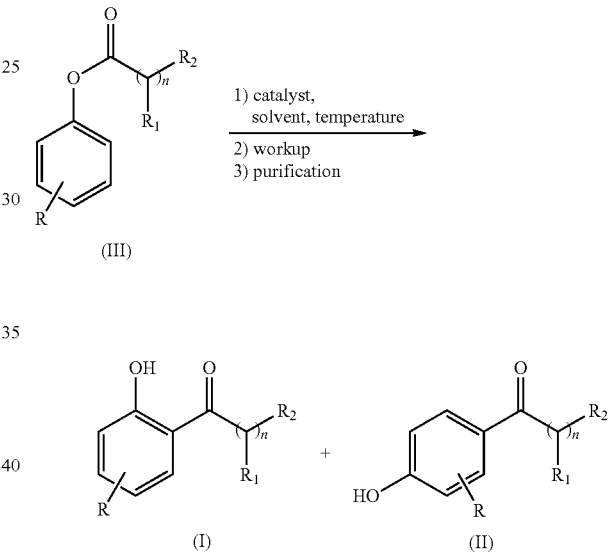

The phenyl esters (III) may be obtained via known esterification protocols, e.g. by reaction of the corresponding phenol with the corresponding acid chloride in a solvent, such as toluene, in the presence of an organic base, such as pyridine, and optionally a nucleophilic catalyst, such as 4-dimethyl amino pyridine. Alternatively, the esterification and Fries-rearrangement steps may be carried out in one step as depicted in Scheme 2 below.

Scheme 2:

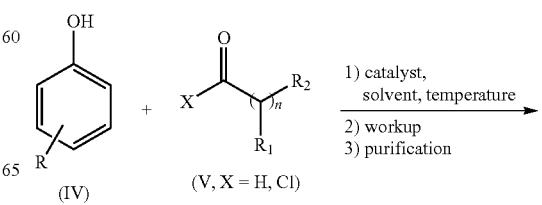

-continued

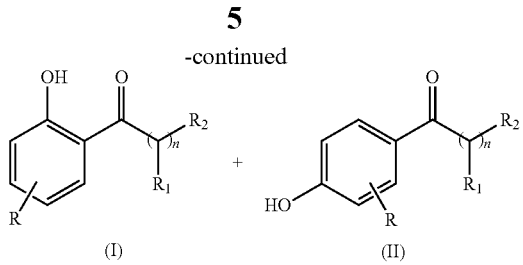

In a final step the reaction product is preferably washed with alkaline aqueous solution, under alkaline conditions (e.g. by extraction with aqueous NaOH solution from 1-2N, preferably 1 N) to remove traces of unreacted starting materials, such as IV and V, which would otherwise olfactorily contaminate the compounds of formula (I). The extraction step also allows removing easily the para-substituted compounds (II), which are undesired side-products formed in varying amounts during the Fries-rearrangement reaction. In certain cases, a product of sufficient olfactory quality might be obtained by careful distillation of the crude product without alkaline extraction.

The invention is now further described with reference to the following non-limiting examples. These examples are for the purpose of illustration only and it is understood that variations and modifications can be made by one skilled in the art.

EXAMPLE 1

1-(2-hydroxyphenyl)-3-phenylpropan-1-one 1-(2-hydroxyphenyl)-3-phenylpropan-1-one form Aldrich (Cat.10,228-8, 97%, 60 g), an unpleasantly smelling yellow powder, was dissolved in toluene (400 ml), and the solution was washed thoroughly with 1 N aq. NaOH solution (100 mL). Thereby, phenols and carboxylic acids were ionized and extracted into the aqueous phase. The organic layer was further washed twice with half-saturated aq. NaCl-solution (200 mL each), then dried over MgSO4, filtered, concentrated in vacuo and further dried at 0.05 mbar/50° C. to yield 58.7 g (98%) of a clear, slightly yellow oil, which was of sufficient olfactory purity for most perfumery applications. Further purification was achieved via two recrystallizations of the compound from toluene/hexane 1:1 at −20° C. to obtain a white powder, melting point 33.5-34.5° C., of high olfactory purity (yield 71%)

Alternatively, the product purified by the aqueous extraction process described above was distilled over a Vigreux-column three times at 135° C./0.05 mbar, yielding 58% of an almost colourless oil of the same olfactory quality as the recrystallized compound.

$^1$H-NMR (CDCl$_3$, 400.1 MHz): 12.30 (s, 1 H), 7.69 (dd, J=1.5, 8.1 Hz, 1 H), 7.42 (ddd, J=1.9, 7.3, 8.5 Hz, 1 H), 7.33-7.25 (m, 2 H), 7.25-7.15 (m, 3 H), 6.96 (dd, J=0.8, 8.3 Hz, 1 H), 6.84 (ddd, J=1.3, 7.1, 8.1 Hz, 1 H), 3.33-3.22 (m, 2 H), 3.09-2.98 (m, 2H).

$^{13}$C-NMR (CDCl$_3$, 100 MHz): 205.3 (s), 162.4 (s), 140.6 (s), 136.2 (d), 129.7 (d), 128.5 (d), 128.3 (d), 126.2 (d), 119.2 (s), 118.8 (d), 118.5 (d), 39.9 (t), 29.9 (t).

MS (EI, 70 eV): 226 (M$^+$, 22), 208 (14), 207 (20), 137 (7), 121 (100), 91 (18), 65 (28), 39 (11).

Odor description: floral, green, salicylate, lindenblossom, ylang.

EXAMPLE 2

(2-hydroxyphenyl)(phenyl)methanone (2-Hydroxyphenyl)(phenyl)methanone from Aldrich (CAS 117-99-7, Aldrich Cat. 10, 316-0, 5.0 g), a unpleasantly smelling oil, was dissolved in toluene (50 ml), and the solution extracted twice with 1 N aq. NaOH-solution. The organic layer was washed with half-saturated aqueous NaCl-solution, dried over MgSO$_4$, filtered, concentrated in vacuo and further dried at 0.05 mbar to yield 4.23 g (85%) of clear, slightly yellow oil, which was further purified by column flash chromatography on silica with toluene to yield 4.0 g of product, which was bulb-to-bulb distilled at 150-170° C./0.06 mbar to yield 3.85 g (77%) of 2-hydroxyphenyl) (phenyl)methanone of good olfactory purity.

$^1$H-NMR (CDCl$_3$, 400.1 MHz): 12.08 (s, 1 H), 7.72-7.66 (m, 2 H), 7.63-7.56 (m, 2 H), 7.55-7.47 (m, 3 H), 7.09 (dd, J=0.8, 8.3 Hz, 1 H), 6.88 (ddd, J=1.1, 7.1, 8.1 Hz, 1 H).

$^{13}$C-NMR (CDCl$_3$, 100 MHz): 201.4 (s), 163.1 (s), 137.8 (s), 136.2 (d), 133.5 (d), 131.8 (d), 129.0 (d), 128.2 (d), 119.0 (s), 118.5 (d), 118.3 (d).

MS (EI, 70 eV): 198 (M$^+$, 72), 197 (100), 121 (57), 105 (30), 77 (45).

Odour description: floral, rosy, green, geranium.

EXAMPLE 3

1-(2-hydroxy-5-methylphenyl)-3-phenylpropan-1-one p-Tolyl 3-phenylpropanoate (13.0 g, 54.1 mmol) was added to aluminium chloride (9.38 g, 70.3 mmol) and the mixture was heated under stirring to 178° C. for 2 h. Heating was removed and toluene was added (30 ml). Stirring was continued for 15 min to obtain a brown solution, which was cooled with an ice bath prior to the careful, dropwise addition of water (30 ml). The resulting biphasic mixture was further stirred until it reached room temperature, then diluted with toluene. The organic layer was washed 3 times with water, then twice with 1N aq. NaOH solution (50 ml). The organic layer was then neutralized by washing three times with half saturated aq. NaCl, then dried over MgSO$_4$ and concentrated in a rotary evaporator to obtain 9.44 g (73%) of crude brown oil, which was short-path distilled at 129° C./0.05 mbar to obtain 1-(2-hydroxy-5-methylphenyl)-3-phenylpropan-1-one (4.39 g, 34%). The product was further purified by column flash chromatography on silica to obtain 3.68 g (28%) of product, which was finally recrystallized from hexane to yield 2.93 g (25%) of product as white crystals, melting point 40.3° C.

$^1$H-NMR (CDCl$_3$, 400.1 MHz): 12.11 (s, 1 H), 7.51 (d, J=1.5 Hz, 1 H), 7.36-7.19 (m, 6 H), 6.89 (d, J=8.3 Hz, 1 H), 3.37-3.28 (m, 2 H), 3.12-3.02 (m, 2 H), 2.28 (s, 3 H).

$^{13}$C-NMR (CDCl$_3$, 100.6 MHz): 205.2 (s), 160.4 (s), 140.8 (s), 137.4 (s), 129.5 (d), 128.6 (d), 128.4 (d), 126.3 (d), 118.9 (d), 118.3 (d), 40.1 (t), 30.0 (t), 20.5 (q).

MS (EI, 70 eV): 240 (M$^+$, 26), 222 (10), 221 (14), 135 (100), 107 (9), 91 (20), 77 (24).

Odour description: floral, green, lily, frangipani, salicylate.

EXAMPLE 4

1-(2-hydroxyphenyl)-3-phenylbutan-1-one

4a) Phenyl 3-phenylbutanoate

To the solution of phenol (8.62 g, 92 mmol) and 4-dimethylaminopyridine (400 mg) in toluene (110 ml) was added pyridine (18.1 g, 229 mmol) and the resulting solution was cooled to 10° C. Then a solution of 3-phenylbutanoyl chloride (20.1 g, 110 mmol) was added dropwise. The resulting mixture was stirred at room temperature for 24 h, and then cooled to 5° C. before the careful addition of 2N aq. HCl-solution (225 ml). The mixture was stirred intensely for 15 min, then diluted with toluene and transferred into a separatory funnel. The aqueous layer was separated and the organic layer washed 4 times with water, then brine and dried over $MgSO_4$. The solvent was removed in a rotary evaporator and the residue short-path distilled at 125-128° C./0.07 mbar to yield 18.52 g (70%) of colourless oil.

$^1$H-NMR ($CDCl_3$, 400.1 MHz): 7.40-7.30 (m, 6 H), 7.30-7.19 (m, 2 H), 6.95-6.90 (m, 2 H), 3.44 (sxt, J=7.3 Hz, 1 H), 2.93-2.80 (m, 2 H), 1.44 (d, J=7.1 Hz, 3 H).

$^{13}$C-NMR ($CDCl_3$, 100.6 MHz): 170.8 (s), 150.6 (s), 145.2 (s), 129.3 (d), 128.6 (d), 126.8 (d), 126.6 (d), 125.7 (d), 121.5 (d), 43.0 (t), 36.8 (d), 21.9 (q).

MS (EI, 70 eV): 240 ($M^+$, 2), 147 (29), 131 (13), 105 (100), 94 (12), 91 (15), 77 (13).

4b) 1-(2-hydroxyphenyl)-3-phenylbutan-1-one

Titanium(IV) chloride (7.89 g, 41.6 mmol) was dissolved in 1,2-dichloroethane (30 ml). To this solution was added dropwise at room temperature the solution of phenyl 3-phenylbutanoate (10 g, 41.6 mmol) in 1,2-dichloroethane (20 ml). The resulting dark brown solution was heated to 130° C. for 6 h, then cooled to 90° C. and toluene (40 ml) was added. The mixture was cooled to 5° C. and water (40 ml) was added carefully to keep the temperature below 10° C. The mixture was then transferred into a separatory funnel, the phases separated and the organic layer washed twice with water, then twice with 1 N aq. NaOH-solution (100 ml), followed by six washes with half saturated brine. The organic layer was dried with $MgSO_4$ and the solvent removed in a rotary evaporator and the residue thoroughly dried to yield 3.82 g (38%) of a dark oil, which was bulb-to-bulb distilled at 170-180° C./0.05 mbar to yield 1.74 g (17%), which was further purified by column flash chromatography on silica to obtain 1.2 g (12%) of product, which was finally recrystallized from hexane/toluene 2:1 to yield 1.1 g (11%) of product as white crystals, melting point 76.8° C.

$^1$H-NMR ($CDCl_3$, 400.1 MHz): 12.34 (s, 1 H), 7.76 (dd, J=1.6, 8.1 Hz, 1 H), 7.47 (ddd, J=1.5, 7.1, 8.5 Hz, 1 H), 7.37-7.26 (m, 4 H), 7.26-7.19 (m, 1 H), 6.99 (dd, J=0.9, 8.3 Hz, 1 H), 6.89 (ddd, J=1.2, 7.1, 8.1 Hz, 1 H), 3.57-3.45 (m, 1 H), 3.35 (dd, J=5.9, 16.2 Hz, 1 H), 3.21 (dd, J=8.1, 16.2 Hz, 1 H), 1.38 (d, J=6.9 Hz, 3 H).

$^{13}$C-NMR ($CDCl_3$, 100.6 MHz): 205.3 (s), 162.6 (s), 146.0 (s), 136.3 (d), 129.9 (d), 128.6 (d), 126.8 (d), 126.4 (d), 119.5 (s), 118.8 (d), 118.6 (d), 46.5 (t), 35.8 (d), 21.9 (q).

MS (EI, 70 eV): 240 ($M^+$, 37), 225 (36), 207 (24), 121 (100), 105 (64).

Odour description: floral, green, salicylate.

EXAMPLE 5

1-(2-hydroxyphenyl)-3-(o-tolyl)propan-1-one

5a) Phenyl 3-(o-tolyl)propanoate

The procedure as described in Example 4a) was repeated with phenol (48 mmol) and 3-o-tolylpropanoyl chloride (55 mmol). The crude product (12.4 g, 97%) was short path distilled at 127-129° C./0.05 mbar to yield 10.6 g (93%) of product as a colourless, semicrystalline oil.

$^1$H-NMR ($CDCl_3$, 400.1 MHz): 7.38-7.30 (m, 2 H), 7.23-7.10 (m, 5 H), 7.05-6.99 (m, 2 H), 3.10-3.02 (m, 2 H), 2.86-2.79 (m, 2 H), 2.35 (s, 3 H).

$^{13}$C-NMR ($CDCl_3$, 100.6 MHz): 171.4 (s), 150.6 (s), 138.2 (s), 136.0 (s), 130.3 (d), 129.3 (d), 128.6 (d), 126.5 (d), 126.1 (d), 125.7 (d), 121.5 (d), 34.6 (t), 28.2 (t), 19.2 (q).

MS (EI, 70 eV): 240 ($M^+$, <1), 147 (36), 119 (38), 105 (100), 94 (23), 91 (13), 77 (14), 65 (14).

5b) 1-(2-hydroxyphenyl)-3-(o-tolyl)propan-1-one

The procedure as described in Example 4b) was repeated with phenyl 3-o-tolylpropanoate (44 mmol). The crude product (5.94 g. 56%) was bulb-to-bulb distilled at 160°-190° C., 0.05 mbar, and the distilled product was recrystallized from hexanes followed by flash chromatography on SiO2 (eluent: toluene) to yield after thorough drying under high vacuum 0.82 g (8%) of white crystalline product, melting poiunt 52.4° C.

$^1$H-NMR ($CDCl_3$, 400.1 MHz): 12.31 (s, 1 H), 7.74 (dd, J=1.8, 8.1 Hz, 1 H), 7.47 (ddd, J=1.8, 7.2, 8.5 Hz, 1 H), 7.21-7.12 (m, 4 H), 6.99 (dd, J=0.9, 8.5 Hz, 1 H), 6.88 (ddd, J=1.3, 7.1, 8.0 Hz, 1 H), 3.31-3.24 (m, 2 H), 3.09-3.02 (m, 2 H), 2.36 (s, 3 H).

$^{13}$C-NMR ($CDCl_3$, 100.6 MHz): 205.5 (s), 162.5 (s), 138.8 (s), 136.4 (d), 136.0 (s), 130.4 (d), 129.8 (d), 128.7 (d), 126.5 (d), 126.2 (d), 119.3 (s), 118.9 (d), 118.6 (d), 38.7 (t), 27.4 (t), 19.3 (q).

MS (EI, 70 eV): 240 ($M^+$, 3), 222 (77), 207 (11), 194 (5), 131 (7), 121 (100), 107 (32), 105 (29), 93 (15), 77 (14), 65 (23).

Odour description: floral green, tropical flower, orchid, salicylate

EXAMPLE 6

1-(2-hydroxyphenyl)-2-methyl-3-phenylpropan-1-one 6a) phenyl 2-methyl-3-phenylpropanoate The procedure as described in Example 4a) was repeated with phenol (30.5 mmol) and 2-methyl-3-phenylpropanoyl chloride (30.5 mmol). The crude product (5.51 g, 75%) was used without further purification in the next step.

$^1$H-NMR ($CDCl_3$, 400.1 MHz): 7.37-7.28 (m, 4 H), 7.27-7.16 (m, 4 H), 6.95-6.89 (m, 2 H), 3.13 (dd, J=7.6, 13.4 Hz, 1 H), 3.00 (sxt, J=7.1 Hz, 1 H), 2.83 (dd, J=7.2, 13.3 Hz, 1 H), 1.32 (d, J=6.8 Hz, 3 H)

$^{13}$C-NMR ($CDCl_3$, 100.6 MHz): 174.6 (s), 150.7 (s), 139.0 (s), 129.3 (d), 129.1 (d), 128.4 (d), 126.5 (d), 125.7 (d), 121.5 (d), 41.6 (d), 39.8 (t), 16.9 (q).

MS (EI, 70 eV): 240 ($M^+$, 4), 147 (33), 119 (48), 91 (100), 77 (6), 65 (12).

6b) 1-(2-hydroxyphenyl)-2-methyl-3-phenylpropan-1-one

The procedure as described in Example 4b) was repeated with phenyl 2-methyl-3-phenylpropanoate (23 mmols). The crude product (3.51 g. 64%) was bulb-to-bulb distilled at 180°-200° C., 0.06 mbar, and the distilled product was purified by flash chromatography on $SiO_2$ (eluent: toluene) to yield, after bulb-to-bulb distillation at 160-170° C./0.05 mbar, 1.13 g (19%) of a colourless oil.

$^1$H-NMR ($CDCl_3$, 400.1 MHz): 12.50 (s, 1 H), 7.74 (dd, J=1.5, 8.1 Hz, 1 H), 7.44 (ddd, J=1.5, 7.0, 8.4 Hz, 1 H), 7.30-7.23 (m, 2 H), 7.22-7.15 (m, 3 H), 6.98 (dd, J=1.0, 8.3 Hz, 1 H), 6.86 (ddd, J=1.3, 7.0, 8.1 Hz, 1 H), 3.79 (sxt, J=8.1 Hz, 1 H), 3.16 (dd, J=6.4, 13.8 Hz, 1 H), 2.73 (dd, J=7.7, 13.8 Hz, 1 H), 1.24 (d, J=6.8 Hz, 3 H).

$^{13}$C-NMR (CDCl$_3$, 100.6 MHz): 209.8 (s), 163.1 (s), 139.4 (s), 136.3 (d), 129.7 (d), 129.0 (d), 128.4 (d), 126.4 (d), 118.8 (d), 118.7 (d), 118.5 (s), 42.1 (d), 39.3 (t), 17.7 (q).

MS (EI, 70 eV): 240 (M$^+$, 22), 225 (4), 207 (5), 121 (100), 93 (9), 91 (19), 77 (4), 65 (14).

Odour description: floral green, anisic watery, slightly medicinal.

EXAMPLE 7

Fragrance Composition for a Shampoo

| Compound/Ingredient | parts by weight 1/1000 |
|---|---|
| Undec-10-enal (at 10% in TEC) | 2 |
| Phenethyl 2-methylbutanoate | 30 |
| Benzyl acetate | 30 |
| 3,7-Dimethyloct-6-en-1-ol (Citronellol) | 60 |
| (E)-1-(2,6,6-Trimethylcyclohexa-1,3-dienyl)but-2-en-1-one (beta-Damascenone) | 2 |
| 1-Phenylethyl acetate (Gardenol) | 20 |
| Methyl 2-(3-oxo-2-pentylcyclopentyl)acetate (Hedione) | 120 |
| Z-3-Hexenol | 4 |
| Z-3-Hexenyl acetate | 4 |
| (Z)-((Z)-Hex-3-enyl) hex-3-enoate | 8 |
| Hex-3-enyl 2-methylbutanoate | 8 |
| Hexyl Acetate | 40 |
| Hexyl Salicylate | 180 |
| Indole (at 1% in TEC) | 70 |
| beta-Ionone | 60 |
| (Z)-3-Methyl-2-(pent-2-enyl)cyclopent-2-enone (cis-Jasmone) | 10 |
| Lemon oil | 60 |
| 2-(5-Methyl-5-vinyltetrahydrofuran-2-yl)propan-2-ol (Linalool oxide) | 10 |
| Linalool | 160 |
| Methyl Anthranilate | 10 |
| Methyl Salicylate (at 10% in DPG) | 4 |
| 4-Methyl-2-(2-methylprop-1-enyl)tetrahydro-2H-pyran (Rose oxide) at 10% in DPG | 8 |
| Dipropylene glycol (DPG) | 70.0 |
| 1-(2-hydroxyphenyl)-3-phenylpropan-1-one (Example 1) | 30.0 |

In this composition, which is added at 1% wt/wt to a hair shampoo base, 1-(2-hydroxyphenyl)-3-phenylpropan-1-one brings a green natural floralcy to the composition and adds volume when assessed on neat and in bloom in water.

The invention claimed is:

1. A fragrance compound of formula (I) or a flavor compound of formula (I)

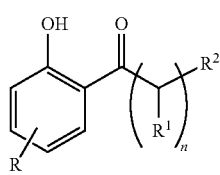

(I)

wherein
R is hydrogen or methyl;
n=2;
R$^1$ is, independently of each other, hydrogen or methyl;
R$^2$ is phenyl wherein the ring is optionally substituted with one or two methyl groups;
and the compound of formula (I) comprises 13 to 18 carbon atoms.

2. The fragrance compound of formula (I) or a flavor compound of formula (I) according to claim 1 which is selected from the group consisting of:
1-(2-hydroxyphenyl)-3-(o-tolyl)propan-1-one,
1-(2-hydroxyphenyl)-2-methyl-3-phenylpropan-1-one,
1-(2-hydroxyphenyl)-3-phenylbutan-1-one,
1-(2-hydroxy-5-methylphenyl)-3-phenylpropan-1-one, and
1-(2-hydroxyphenyl)-3-phenylpropan-1-one.

3. A method of improving, enhancing, or modifying a consumer product base comprising the step of:
Including within the consumer product base at least one compound of formula (I) according to claim 1

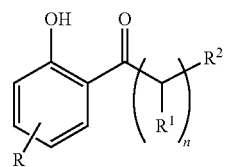

(I)

wherein
R is hydrogen or methyl;
n=2;
R$^1$ is, independently of each other, hydrogen or methyl;
R$^2$ is phenyl wherein the ring is optionally substituted with one or two methyl groups;
and the compound of formula (I) comprises 13 to 18 carbon atoms.

4. A fragrance composition comprising
a) at least one compound of formula (I) according to claim 1

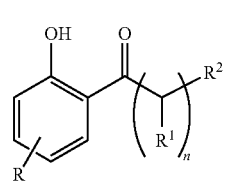

(I)

wherein
R is hydrogen or methyl;
n=2;
R$^1$ is, independently of each other, hydrogen or methyl;
R$^2$ is phenyl wherein the ring is optionally substituted with one or two methyl groups; and the compound of formula (I) comprises 13 to 18 carbon atoms;
b) and at least one further odorant or flavor.

5. A fragranced article comprising
a) at least one compound of formula (I) according to claim 1

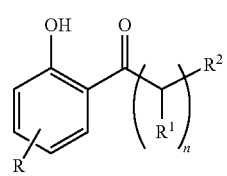

(I)

wherein

R is hydrogen or methyl;

n=2;

R¹ is, independently of each other, hydrogen or methyl;

R² is phenyl wherein the ring is optionally substituted with one or two methyl groups; and the compound of formula (I) comprises 13 to 18 carbon atoms;

b) and a consumer product base.

6. An fragranced article according to claim 5 wherein the consumer product base comprises ethanol.

7. An article according to claim 5 wherein the fragranced article is selected from the group consisting of personal care products, home care products, laundry care products and fine perfumery.

8. An article according to claim 6 wherein the fragranced article is selected from the group consisting of personal care products, home care products, laundry care products and fine perfumery.

9. A flavored article comprising
a) at least one compound of formula (I) according to claim 1

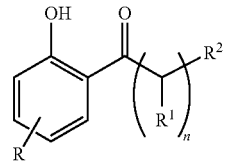

(I)

wherein

R is hydrogen or methyl;

n=2;

R¹ is, independently of each other, hydrogen or methyl;

R² is phenyl wherein the ring is optionally substituted with one or two methyl groups; and the compound of formula (I) comprises 13 to 18 carbon atoms.

\* \* \* \* \*